US008071028B2

(12) United States Patent
Andrews et al.

(10) Patent No.: US 8,071,028 B2
(45) Date of Patent: Dec. 6, 2011

(54) METHOD AND APPARATUS FOR PROVIDING POWER MANAGEMENT IN DATA COMMUNICATION SYSTEMS

(75) Inventors: Tae Wan Andrews, Oakland, CA (US); Stephen C. Bubrick, Orinda, CA (US); Sheilah S. Estoesta, Mountain View, CA (US); Brad D. Etter, Fremont, CA (US); Hyong Yoon Park, San Francisco, CA (US); Gene Ming Pon, San Jose, CA (US); Christopher V. Reggiardo, Castro Valley, CA (US); Heber Saravia, Daly City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1113 days.

(21) Appl. No.: 10/861,626

(22) Filed: Jun. 4, 2004

(65) Prior Publication Data
US 2005/0009126 A1 Jan. 13, 2005

Related U.S. Application Data

(60) Provisional application No. 60/478,436, filed on Jun. 12, 2003.

(51) Int. Cl.
*G01N 33/00* (2006.01)
(52) U.S. Cl. ....... 422/68.1; 422/50; 422/82.05; 422/104
(58) Field of Classification Search ................. 422/68.1, 422/50, 82.05, 104; 364/413.02
See application file for complete search history.

(56) References Cited

U.S. PATENT DOCUMENTS

| 3,930,493 | A |   | 1/1976  | Williamson      |         |
|-----------|---|---|---------|-----------------|---------|
| 4,018,547 | A |   | 4/1977  | Rogen           |         |
| 4,121,282 | A |   | 10/1978 | Ohsawa          |         |
| 4,439,197 | A |   | 3/1984  | Honda et al.    |         |
| 4,531,235 | A |   | 7/1985  | Brusen          |         |
| 4,866,396 | A |   | 9/1989  | Tamura          |         |
| 4,984,581 | A |   | 1/1991  | Stice           |         |
| 5,004,532 | A |   | 4/1991  | Hale            |         |
| 5,019,974 | A | * | 5/1991  | Beckers         | 600/316 |
| 5,051,880 | A |   | 9/1991  | Harm et al.     |         |
| 5,079,920 | A |   | 1/1992  | Whitehead et al.|         |

(Continued)

FOREIGN PATENT DOCUMENTS
EP 0455455 11/1991
(Continued)

OTHER PUBLICATIONS

"An Electrochemical Slow Flow Meter", http://gore.ocean.washington.edu/research/slow_flow_meter.html, Feb. 10, 2005, 3 pages.

(Continued)

*Primary Examiner* — Sam P Siefke
(74) *Attorney, Agent, or Firm* — Jackson & Co., LLP

(57) ABSTRACT

A blood glucose meter having a compact housing, a display unit disposed on the housing, the display unit including a display light source to illuminate the display unit, an input unit disposed on the housing, the input unit configured to provide input functions for the blood glucose meter, and a power source provided within the housing for providing power to the blood glucose meter, where the housing includes a port integrated on said housing configured to receive a blood glucose test strip, and corresponding methods of measuring blood glucose meter is provided.

54 Claims, 6 Drawing Sheets

U.S. PATENT DOCUMENTS

| | | |
|---|---|---|
| 5,081,421 A | 1/1992 | Miller et al. |
| 5,124,661 A | 6/1992 | Zelin et al. |
| 5,207,666 A | 5/1993 | Idriss et al. |
| 5,211,371 A | 5/1993 | Coffee |
| 5,211,626 A | 5/1993 | Frank et al. |
| 5,278,997 A | 1/1994 | Martin |
| 5,325,280 A * | 6/1994 | Tortola et al. ............... 362/234 |
| 5,366,292 A | 11/1994 | Voss |
| 5,391,250 A | 2/1995 | Cheney, II et al. |
| 5,404,585 A | 4/1995 | Vimpari et al. |
| 5,507,288 A | 4/1996 | Bocker et al. |
| 5,568,400 A | 10/1996 | Stark et al. |
| 5,575,770 A | 11/1996 | Melsky et al. |
| 5,604,404 A | 2/1997 | Sahara |
| 5,622,413 A | 4/1997 | Kim et al. |
| 5,622,482 A | 4/1997 | Lee |
| 5,645,709 A | 7/1997 | Birch et al. |
| 5,661,643 A | 8/1997 | Blakely et al. |
| 5,695,949 A | 12/1997 | Galen et al. |
| 5,703,928 A | 12/1997 | Galloway et al. |
| 5,822,715 A * | 10/1998 | Worthington et al. ......... 702/19 |
| 5,848,990 A | 12/1998 | Cirelli et al. |
| 5,899,855 A * | 5/1999 | Brown ........................ 600/301 |
| 5,913,833 A | 6/1999 | Elstrom et al. |
| 6,027,459 A | 2/2000 | Shain et al. |
| 6,027,496 A | 2/2000 | Loomis et al. |
| 6,027,692 A | 2/2000 | Galen et al. |
| 6,059,546 A | 5/2000 | Brenan et al. |
| 6,063,039 A | 5/2000 | Cunningham et al. |
| 6,067,463 A | 5/2000 | Jeng et al. |
| 6,071,249 A | 6/2000 | Cunningham et al. |
| 6,071,251 A | 6/2000 | Cunningham et al. |
| 6,073,031 A | 6/2000 | Helstab et al. |
| 6,077,660 A | 6/2000 | Wong et al. |
| 6,081,104 A | 6/2000 | Kern |
| 6,085,871 A | 7/2000 | Karamata |
| 6,093,156 A | 7/2000 | Cunningham et al. |
| 6,129,823 A | 10/2000 | Hughes et al. |
| 6,132,371 A | 10/2000 | Dempsey et al. |
| 6,144,303 A | 11/2000 | Federman |
| 6,144,922 A | 11/2000 | Douglas et al. |
| 6,155,992 A | 12/2000 | Henning et al. |
| 6,160,449 A | 12/2000 | Klomsdorf et al. |
| 6,162,202 A | 12/2000 | Sicurelli et al. |
| 6,173,160 B1 | 1/2001 | Liimatainen |
| 6,175,752 B1 | 1/2001 | Say et al. |
| 6,185,452 B1 | 2/2001 | Schulman et al. |
| 6,206,841 B1 | 3/2001 | Cunningham et al. |
| 6,208,894 B1 | 3/2001 | Schulman et al. |
| 6,242,961 B1 | 6/2001 | Liu et al. |
| 6,245,060 B1 | 6/2001 | Loomis et al. |
| 6,248,067 B1 | 6/2001 | Causey, III et al. |
| 6,262,708 B1 | 7/2001 | Chu |
| 6,283,926 B1 | 9/2001 | Cunningham et al. |
| 6,295,506 B1 | 9/2001 | Heinonen et al. |
| 6,298,255 B1 | 10/2001 | Cordero et al. |
| 6,306,104 B1 | 10/2001 | Cunningham et al. |
| 6,312,888 B1 | 11/2001 | Wong et al. |
| 6,315,721 B2 | 11/2001 | Schulman et al. |
| 6,368,274 B1 | 4/2002 | Van Antwerp et al. |
| 6,375,638 B2 | 4/2002 | Nason et al. |
| 6,377,894 B1 | 4/2002 | Deweese et al. |
| 6,403,944 B1 | 6/2002 | MacKenzie et al. |
| 6,417,074 B2 | 7/2002 | Kopley et al. |
| 6,425,829 B1 | 7/2002 | Julien |
| 6,427,088 B1 | 7/2002 | Bowman, IV et al. |
| 6,437,379 B2 | 8/2002 | Kopley et al. |
| 6,438,385 B1 | 8/2002 | Heinonen et al. |
| 6,466,807 B1 | 10/2002 | Dobson et al. |
| 6,471,980 B2 | 10/2002 | Sirhan et al. |
| 6,492,180 B2 | 12/2002 | Brown et al. |
| 6,506,168 B1 | 1/2003 | Fathallah et al. |
| 6,514,460 B1 | 2/2003 | Fendrock |
| 6,522,530 B2 | 2/2003 | Bang |
| 6,526,298 B1 | 2/2003 | Khalil et al. |
| 6,540,891 B1 | 4/2003 | Stewart et al. |
| 6,551,276 B1 | 4/2003 | Mann et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,565,738 B1 | 5/2003 | Henning et al. |
| 6,569,157 B1 | 5/2003 | Shain et al. |
| 6,571,128 B2 | 5/2003 | Lebel et al. |
| 6,577,899 B2 | 6/2003 | Lebel et al. |
| 6,582,393 B2 | 6/2003 | Sage, Jr. |
| 6,585,644 B2 | 7/2003 | Lebel et al. |
| 6,586,971 B1 | 7/2003 | Naffziger et al. |
| 6,600,997 B2 | 7/2003 | Deweese et al. |
| 6,615,061 B1 | 9/2003 | Khalil et al. |
| 6,615,074 B2 | 9/2003 | Mickle et al. |
| 6,641,533 B2 | 11/2003 | Causey, III et al. |
| 6,648,821 B2 | 11/2003 | Lebel et al. |
| 6,659,948 B2 | 12/2003 | Lebel et al. |
| 6,669,669 B2 | 12/2003 | Flaherty et al. |
| 6,679,841 B2 | 1/2004 | Bojan et al. |
| 6,687,546 B2 | 2/2004 | Lebel et al. |
| 6,692,457 B2 | 2/2004 | Flaherty |
| 6,694,191 B2 | 2/2004 | Starkweather et al. |
| 6,723,072 B2 | 4/2004 | Flaherty et al. |
| 6,730,200 B1 | 5/2004 | Stewart et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,840,912 B2 | 1/2005 | Kloepfer et al. |
| 6,859,831 B1 | 2/2005 | Gelvin et al. |
| 6,862,465 B2 | 3/2005 | Shults et al. |
| 6,873,268 B2 | 3/2005 | Lebel et al. |
| 6,931,327 B2 | 8/2005 | Goode, Jr. et al. |
| 6,950,708 B2 | 9/2005 | Bowman IV et al. |
| 6,958,129 B2 | 10/2005 | Galen et al. |
| 6,958,705 B2 | 10/2005 | Lebel et al. |
| 6,974,437 B2 | 12/2005 | Lebel et al. |
| 6,990,372 B2 | 1/2006 | Perron et al. |
| 7,003,340 B2 | 2/2006 | Say et al. |
| 7,020,508 B2 | 3/2006 | Stirovic et al. |
| 7,024,245 B2 | 4/2006 | Lebel et al. |
| 7,024,249 B2 | 4/2006 | Weisner et al. |
| 7,041,468 B2 | 5/2006 | Drucker et al. |
| 7,043,287 B1 | 5/2006 | Khalil et al. |
| 7,067,498 B2 | 6/2006 | Wolf et al. |
| 7,098,803 B2 | 8/2006 | Mann et al. |
| 7,123,206 B2 | 10/2006 | Hess et al. |
| 7,136,704 B2 | 11/2006 | Schulman |
| 7,153,212 B1 * | 12/2006 | Karten et al. .................. 463/47 |
| 7,154,398 B2 | 12/2006 | Chen et al. |
| 7,186,566 B2 | 3/2007 | Qian |
| 7,202,734 B1 | 4/2007 | Raab |
| 7,205,409 B2 | 4/2007 | Pei et al. |
| 7,225,535 B2 | 6/2007 | Feldman et al. |
| 7,258,666 B2 | 8/2007 | Brown |
| 7,266,400 B2 | 9/2007 | Fine et al. |
| 2001/0023095 A1 | 9/2001 | Kopley et al. |
| 2001/0024864 A1 | 9/2001 | Kopley et al. |
| 2002/0118090 A1 | 8/2002 | Park et al. |
| 2002/0193679 A1 | 12/2002 | Malave et al. |
| 2003/0060765 A1 * | 3/2003 | Campbell et al. ............. 604/131 |
| 2003/0078560 A1 | 4/2003 | Miller et al. |
| 2003/0107487 A1 | 6/2003 | Korman et al. |
| 2003/0198558 A1 | 10/2003 | Nason et al. |
| 2003/0212346 A1 | 11/2003 | Yuzhakov et al. |
| 2004/0019321 A1 | 1/2004 | Sage et al. |
| 2004/0064133 A1 | 4/2004 | Miller et al. |
| 2004/0132220 A1 | 7/2004 | Fish |
| 2004/0133092 A1 | 7/2004 | Kain |

| | | | |
|---|---|---|---|
| 2004/0152622 A1 | 8/2004 | Keith et al. | |
| 2004/0186365 A1 | 9/2004 | Yin et al. | |
| 2005/0038680 A1 | 2/2005 | McMahon | |
| 2005/0053365 A1 | 3/2005 | Adams et al. | |
| 2005/0065464 A1 | 3/2005 | Talbot et al. | |
| 2005/0235732 A1 | 10/2005 | Rush | |
| 2005/0182306 A1 | 11/2005 | Sloan | |
| 2005/0249606 A1 | 11/2005 | Rush | |
| 2006/0001551 A1 | 1/2006 | Kraft et al. | |
| 2006/0247508 A1 | 11/2006 | Fennell | |

FOREIGN PATENT DOCUMENTS

| | | |
|---|---|---|
| EP | 0878707 | 11/1998 |
| EP | 0543916 | 7/2001 |
| EP | 1130638 | 9/2001 |
| JP | 2001-177423 | 6/2001 |
| JP | 2001-056673 | 11/2001 |
| WO | WO-02/084860 | 10/2002 |
| WO | WO-2004/028337 | 4/2004 |
| WO | WO-2005/101994 | 11/2005 |
| WO | WO-2006/079114 | 7/2006 |
| WO | WO-2006/110913 | 10/2006 |
| WO | WO-2006/113408 | 10/2006 |
| WO | WO-2006/113521 | 10/2006 |

OTHER PUBLICATIONS

Barbosa, R. M., "Electrochemical Studies of Zinc in Zinc-Insulin Solution", *Journal of the Royal Society of Chemistry, Analyst 121*(12), CAPLUS Abstract, 1996, pp. 1789-1793.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, Jan. 1996, pp. 165-194.

\* cited by examiner

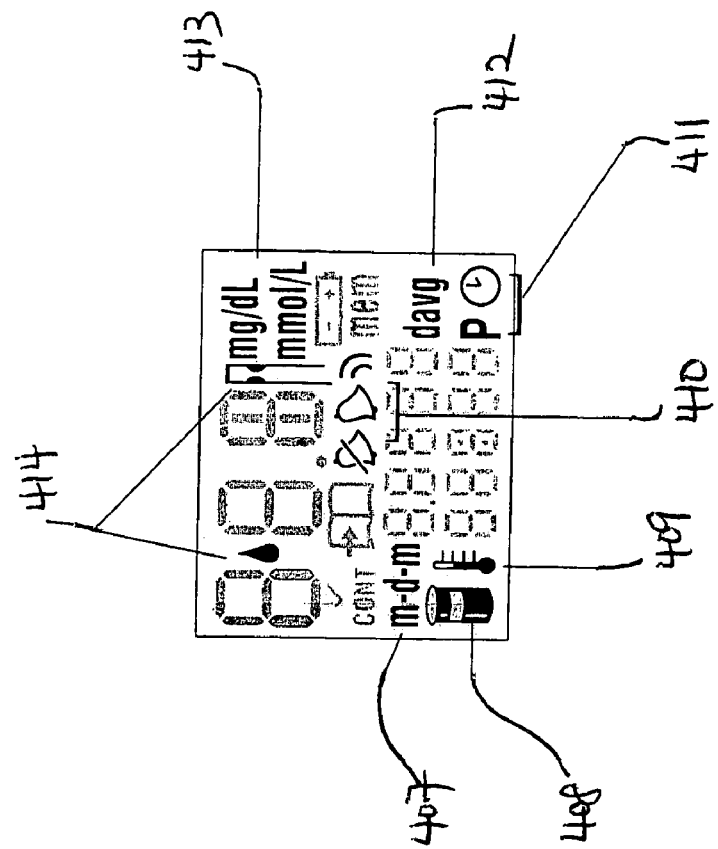
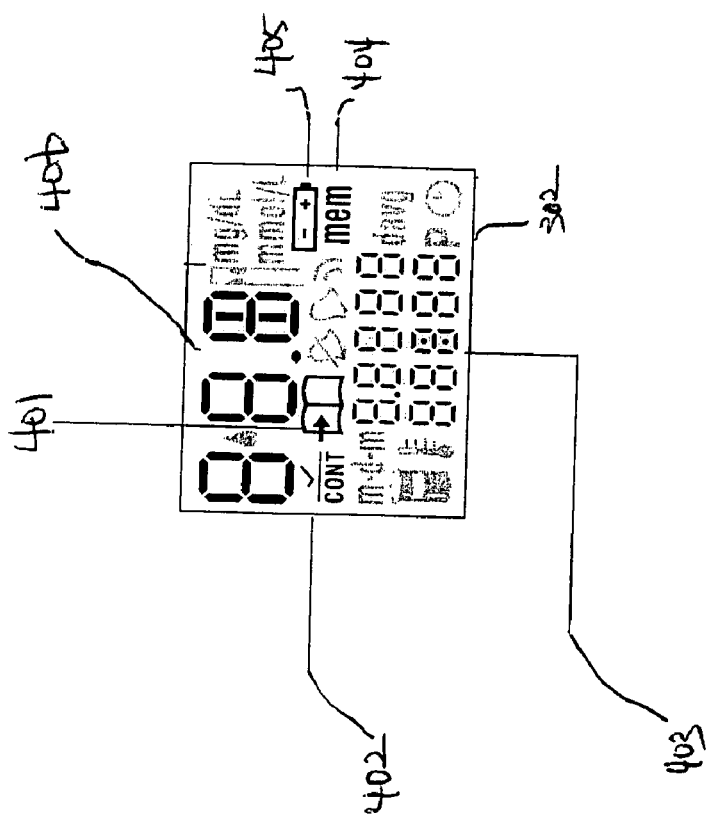
Figure 4B
Figure 4A

METHOD AND APPARATUS FOR PROVIDING POWER MANAGEMENT IN DATA COMMUNICATION SYSTEMS

RELATED APPLICATION

This application claims priority under 35 USC §119 to Provisional patent application Ser. No. 60/478,436 filed on Jun. 12, 2003, entitled "Method and Apparatus for Providing Power Management in Data Communication Systems", the disclosure of which is incorporated herein by reference for all purposes.

BACKGROUND

The present invention relates to data monitoring systems. More specifically, the present invention relates to portable analyte monitoring systems. More specifically, the present invention relates to a compact, blood glucose meter for use in a glucose monitoring system to self-monitor glucose level in whole blood, as an aid to disease management, and also by healthcare professionals as an aid to monitor the effectiveness of diabetes treatment.

SUMMARY OF THE INVENTION

The market for glucose monitoring systems in the United States as well as globally is rapidly increasing, as better health education and early detection of diabetic conditions through regular check ups have increased the percentage of the diabetic population who undertake the task of monitoring their diet and daily activities based on the detected level of blood glucose using glucose monitoring systems. One group of such rapidly increasing segment of the population is children with diabetic conditions who are advised to monitor their blood glucose levels.

While miniaturization has been a factor of recent designs in the glucose monitoring systems and the glucose meters, the physical constraints of the components of such systems have established a certain size limitation. As such, the larger and bulkier the device, the less desirable and convenient for the device to be carried around or used and operated by the patients, especially children.

In view of the foregoing, in accordance with the various embodiments of the present invention, there is provided a blood glucose meter which is designed to be substantially more compact than presently available commercial blood glucose meters, which configuration that is much more amenable to usage and portage by younger diabetic patients such as children.

More specifically, in one aspect of the invention, the blood glucose meter is configured to include a LCD backlight and a flashlight features which will assist the patient in reading the metered glucose level in low-light testing areas such as in theaters, low ambient light restaurants, areas, outdoors during non-daylight times and so on, as well as a light source to guide the insertion and removal of the test strip, which may include the usage of a light emitting diode. Indeed, as the light source (e.g., the LED) may be pulsed and still display substantially the same light output as one which is turned on in steady state, the battery life of the glucose meter device may be prolonged since the pulsed LED light source requires significantly less power (and thus draining the battery at a much slower rate) than when the LED light source is maintained at the on position. Indeed, in one embodiment, the central processing unit of the glucose meter device may be configured to control the switching on and off of the light source as well as the level of light intensity by, for example, adjusting the duty cycle and the period during which the light source is configured to be turned on.

Additionally, in accordance with a further aspect of the invention, the blood glucose meter may include a numerically displayed clock with a date display which may be visible when the meter is not in use. Moreover, the clock feature in yet a further embodiment of the present invention may include an alarm which would allow the users to set alarm reminder for performing blood glucose level testing, where the alarm feature may include one or a combination of an auditory alarm, a visual alarm alert, and a vibration alert mode.

Indeed, a blood glucose meter in accordance with one embodiment of the present invention includes a compact housing for a blood glucose meter, a display unit disposed on the housing, the display unit configured to display information related to the blood glucose meter, an input unit disposed on the housing, the input unit configured to provide input functions for the blood glucose meter, and a power source provided within the housing for providing power to the blood glucose meter.

The display unit may include one of a liquid crystal display (LCD), a touch sensitive screen, and a plasma display unit.

The display unit may also include a light source to illuminate the display unit, where the light source may be configured to provide a backlight function and a flashlight function of the display unit.

The light source in one embodiment may be configured to be pulsed at a frequency greater than 60-100 Hertz. Moreover, the light source may further configured to have a peak wavelength of approximately 570 nanometers.

In one embodiment, the light source may include a light emitting diode (LED), and more specifically, a yellow-green LED.

In a further embodiment, the housing may include a port integrated on the housing configured to receive a blood glucose test strip.

The port may include a light source that may be configured to substantially illuminate the port to assist in the insertion and/or removal of the blood glucose test strip.

In yet another embodiment, the display unit may be configured to illuminate upon detection of a blood glucose test strip insertion into the port. Further, the display unit may be configured to remain illuminated until the test strip is removed from the port.

The input unit in one embodiment may include an on/off switch.

A blood glucose meter in accordance with another embodiment includes a compact housing for a blood glucose meter, a display unit disposed on the housing, the display unit including a display light source to illuminate the display unit, an input unit disposed on the housing, the input unit configured to provide input functions for the blood glucose meter, and a power source provided within the housing for providing power to the blood glucose meter, where the housing includes a port integrated on said housing configured to receive a blood glucose test strip.

The port in one embodiment may include a port light source, the port light source configured to substantially illuminate the port to assist in the insertion and/or removal of the blood glucose test strip.

Additionally, in an alternate embodiment, the port light source may be integrated with the display light source.

A method of measuring blood glucose level in accordance with yet another embodiment of the present invention includes the steps of providing a compact housing, disposing a display unit on the housing, the display unit including a display light source to illuminate the display unit, disposing an input unit on the housing, the input unit configured to provide input functions for the blood glucose meter, providing a power source within the housing for providing power to the blood glucose meter, where the housing includes a port integrated on said housing configured to receive a blood glucose test strip.

These and other features and advantages of the present invention will be understood upon consideration of the following detailed description of the invention and the accompanying drawings.

INCORPORATION BY REFERENCE

Applicants herein incorporate by reference application Ser. No. 09/434,026 filed Nov. 4, 1999 entitled "Small Volume In Vitro Analyte Sensor and Methods", application Ser. No. 09/753,746 filed on Jan. 2, 2001 entitled "Analyte Monitoring Device and Methods of Use", and Provisional application Ser. No. 60/437,374 filed Dec. 31, 2002 and application Ser. No. 10/745,878 filed Dec. 26, 2003 both entitled "Continuous Glucose Monitoring System and Methods of Use", each assigned to the Assignee of the present application for all purposes.

BRIEF DESCRIPTION OF THE DRAWINGS

FIGS. 4A and 4B illustrate the display screen of the glucose meter device in accordance with one embodiment of the present invention;

DETAILED DESCRIPTION

Figure 1:
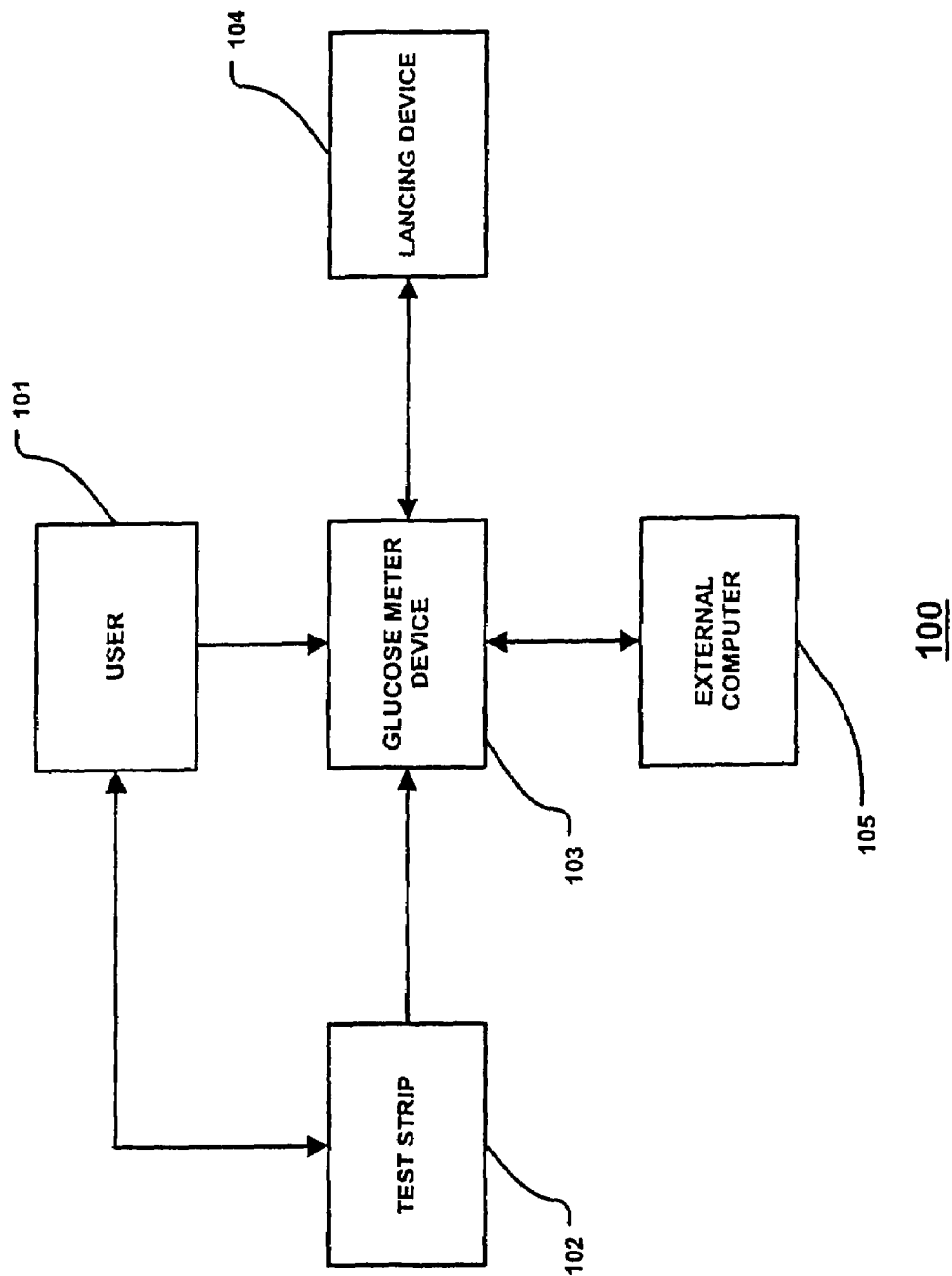
FIG. 1 is a block diagram illustrating an overall glucose monitoring system in accordance with one embodiment of the present invention.

FIG. 1 is a block diagram illustrating an overall glucose monitoring system in accordance with one embodiment of the present invention. Referring to the Figure, the glucose monitoring system 100 in accordance with one embodiment includes a glucose meter device 103 configured to receive a test strip 102 which is used to collect the blood sample for determining the blood glucose level of the user 101. The lancing device 104 is used to draw the blood sample from the user 101 to be collected onto the test strip 102. In one embodiment, the lancing device 104 may be used on the user's fingers, forearm, upper arm, hand, thigh or calf, for example. Moreover, the glucose meter device 103 and the system 100 is configured such that a very small blood sample size such as, for example, approximately 0.3 microliter of sample blood, is necessary to determine a corresponding blood glucose level.

As can be further seen from FIG. 1, the glucose meter device 103 may be operatively coupled to an external computer 105 which may include, in one embodiment, a server terminal connected to a data network, a stand along desktop or laptop computer for use by the user's physician or care provider (or the user herself), a personal digital assistant (PDA) which is operatively configured to store and/or further, to communicate with a data network to transmit and receive patient data related to the glucose level detected from the collected blood sample, for further diagnosis, analysis and the like.

In one embodiment, the user 101 may provide the configuration parameters as well as calibration code to the glucose meter device 103, while the glucose meter device 103 may be configured to output signal prompts to the user 101 such as to indicate a sample fill signal and a sample result signal, and further, to output display the resulting measured blood glucose level from the sampled blood from the user 101. Furthermore, after the user 101 is lanced with the lancing device 104 to generate sufficient amount of sample blood, the test strip 102 is provided in contact thereto (i.e., to the sample blood) while the test strip 102 is operatively coupled to the glucose meter device 103. In this manner, the glucose meter device 103 may in one embodiment be configured to alert the user that the amount of blood sample on the test strip 102 is sufficient to determine the corresponding blood glucose level.

In one aspect of the present invention, the glucose meter device 103 may be configured to make clinical measurements of glucose in whole blood in the range for approximately 20 to 500 mg/dL. Furthermore, as discussed in further detail below, the glucose meter device 103 may be configured to include a display unit which is configured to operate as a user interface to visually interact with the user 101 to prompt for data input, or alternatively, to provide information to the user 101 corresponding to the user's operation of one or more functions of the glucose meter device 103. In one embodiment, the display unit of the glucose meter device 103 may include a LCD display screen which may further be configured, in an alternate embodiment to include a touch-sensitive pad so as to allow the user 101 to input data therethrough. Moreover, in a further embodiment of the present invention, the display unit of the glucose meter device 103 may be configured to include a backlight feature which would permit the user 101 to operate the glucose meter device 103 in a dark ambient setting such as in a theater, outdoor at night, and the like.

Figure 2:
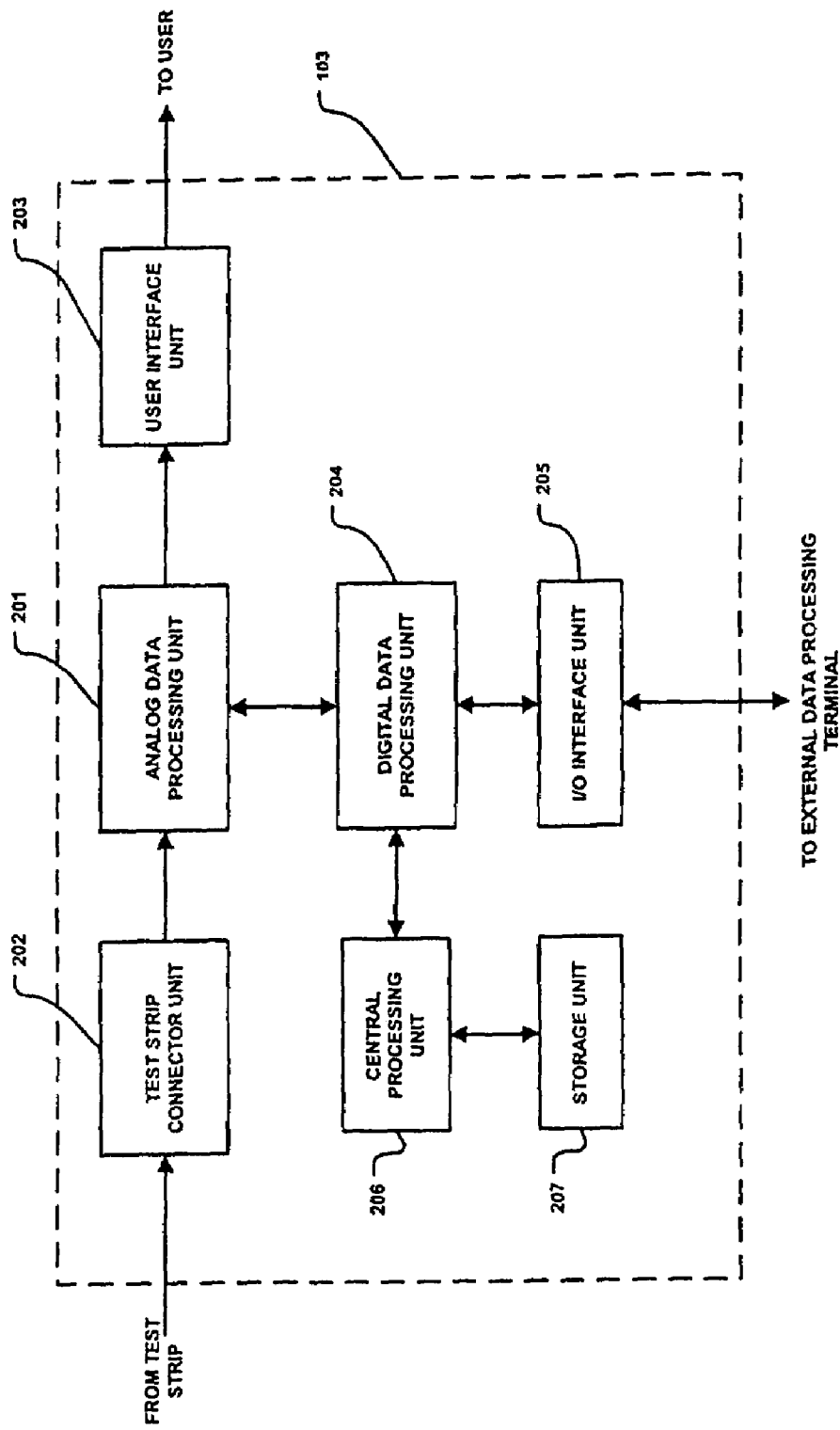
FIG. 2 is a block diagram illustrating a glucose meter device shown in FIG. 1 in accordance with one embodiment of the present invention.

FIG. 2 is a block diagram illustrating a glucose meter device shown in FIG. 1 in accordance with one embodiment of the present invention. Referring to FIG. 2, the glucose meter device 103 in accordance with one embodiment of the present invention includes a central processing unit 206 operatively coupled to a digital data processing unit 204. The central processing unit 206 is further operatively coupled to a storage unit 207 which, in one embodiment, may include one or more of a data storage unit, a random access memory unit and a read-only memory unit. As can be further seen from the Figure, the digital data processing unit 204 is further operatively coupled to an input/output (I/O) interface unit 205 which, in one embodiment, is configured to interface with the external computer 105 (FIG. 1).

Moreover, in the glucose meter device 103, there is provided an analog data processing unit 201 which is configured to detect and process analog signals and which is further operatively coupled to the digital data processing unit 204 for digital data processing of the detected and processed analog signals received from the analog data processing unit 201 in one embodiment of the present invention. Referring back to FIG. 2, the analog data processing unit 201 of the glucose meter device 103 is further configured to operatively couple to a test strip connector unit 202 which is configured to engage with a test strip 102 (FIG. 1) when inserted into the glucose meter device 103. Thereafter, the analog data processing unit 201 as mentioned above is configured to detect the signal level from the collected blood sample received from the test strip 102 (FIG. 1) via the test strip connector unit 202, and to transmit that detected and analog processed data to the digital data processing unit 204 for further data processing.

Referring yet again to FIG. 2, there is also shown a user interface unit 203 provided to the glucose meter device 103. As can be seen, the user interface unit 203 is operatively coupled to the user 101 (FIG. 1) to receive input data or instructions therefrom, or alternatively, to output the processed and/or generated information to the user 101. More specifically, in accordance with one embodiment of the present invention, the user interface unit 203 may include a display unit, an input device such as an input keypad, or any other equivalent device which may provide substantially the same functionality as the input device such as an input keypad.

Additionally, the display unit of the user interface unit 203 may include an LCD display unit which is also capable of providing backlighting so as to permit the user to view the displayed information on the backlit display unit of the user interface unit 203 in dark ambient settings. Moreover, in an alternate embodiment of the present invention, the user interface unit 203 may also include a flashlight feature which, upon activation by the user, is configured to emit a consistent light beam to assist the user in the operation of the glucose meter device 103 and/or the lancing device 104 in dark surroundings. Further, the flashlight feature may also be configured to include a timer function such that the flashlight is configured, in one embodiment, to automatically turn off after a predetermined period of time has elapsed. In this manner, the power source for the glucose meter device 103 (FIG. 1) may be conserved in the cases where the user 101 leaves the flashlight feature on the glucose meter device 103 on.

Referring yet again to FIG. 2, the user interface unit 203 in accordance with a further embodiment of the present invention may include a speaker unit configured to output audio signals. More specifically, in one aspect of the present invention, the user 101 may be alerted or reminded of one or more time specific events or reminder such as the next time the user 101 needs to take a blood glucose level measurement. Rather than relying solely upon the user's memory, the glucose meter device 103 may be configured with an alarm feature operatively engaged with a timer function such that, in addition to displaying the current time information on the display unit, the glucose meter device 103 may be configured to generate and output an audible sound for each specific event or reminder which the user 101 has pre-programmed into the glucose meter device 103. Moreover, in a further embodiment, the audible alarm output (or a series or audible tones as may be selected by the user) may be simultaneously generated with the backlight feature of the glucose meter device 103 such that for each of use, the user is able to view information displayed on the display unit of the user interface unit 203 substantially immediately without the need to perform extra steps such as turning on the backlight function of the glucose meter device 103. In the preferred embodiment, the meter allows the user to set up to four separate alarms to go off every 24 hours at a particular time to remind the user to test her blood glucose level. Preferably, the volume of each alarm may be set independently.

Referring back yet again to FIG. 2, in one embodiment of the present invention, the central processing unit 206 is configured to perform a plurality of functions to maintain, calibrate and operate the glucose meter device 103. More specifically, upon power up of the glucose meter device 103 when the power source such as the batteries, are placed in the respective section of the device housing, under the control of the central processing unit 206, the glucose meter device 103 is configured to perform a power on/reset sequence to initialize the various aforementioned components of the glucose meter device 103 to the necessary configuration settings. Upon successful completion of the power on/reset sequence, the central processing unit 206 is then configured to enter the glucose meter device 103 into a default operation mode (for example, the clock mode) as discussed in further detail below. More specifically, in one embodiment, the central processing unit 206 is configured to access the storage unit 207 to retrieve the corresponding power on/reset sequence instruction set from the storage unit 207 (for example, in the ROM portion and/or the RAM portion thereof). Moreover, in one embodiment, the central processing unit 206 is configured to perform and complete the aforementioned power on/reset sequence within approximately 500 mseconds.

In one aspect, the central processing unit 206 of the glucose meter device 103 may be configured for operating the meter device 103 in one of the following modes of operation—the clock mode (the default mode discussed above), the test mode, the configuration mode, and the measurement log review mode. The default clock mode is configured in one embodiment to display the time/date information as configured by the user 101. The test mode includes operations for the user to perform blood glucose measurements, the configuration mode includes functions for the user to select user preferences for configurable parameters of the glucose meter device 103, and the measurement log review mode allows reviewing of the glucose measurements stored in the meter device 103.

In one embodiment, when the glucose meter device 103 enters a non-clock mode of operation, the meter device 103 may be configured to display a self-test screen that illuminates all segments of the display unit in the user interface unit 203 prior to operating in the selected mode of operation. Moreover, the glucose meter device 103 may be configured to exit all operation modes after exceeding a predetermined period of non-activity/idle time (for example, 2 minutes) such as no switch activity, test strip activity, or display activity, for example.

Additionally, the central processing unit 206 of the glucose meter device 103 is configured such that, upon detection that there was a loss of power (for example, battery removal), the internal date is set to the last recorded date, and in the case where there is no valid recorded dates, the central processing unit 206 is configured to set the internal date to a predetermined date such as Jan. 1, 2002, for example. Likewise, upon detection of the loss of power, the internal time in one embodiment is reset to 12:00 am until a further time when the user resets the internal time. Moreover, the blood sample test data collected during the period of power loss is configured to be flagged with a "lost time" flag and the corresponding lost power internal date and time discussed above. Upon re-application of power to the glucose meter device 103, in one embodiment, the user may be prompted (e.g., blinking signals displayed on the user interface unit 203) to reset the time and date information in the default clock mode.

Referring still again to FIG. 2, in the test mode of operation of the glucose meter device 103 in one embodiment, the correct insertion of the test strip 102 (FIG. 1) engaged into the test strip connector unit 202 of the meter device 103 is detected, and upon removal of the test strip 102, the meter device 103 is configured to enter the default operation mode. In this manner, the glucose meter device 103 may be configured to automatically enter into the test mode of operation upon the correct insertion of the test strip 102. Alternatively, the glucose meter device 103 may be configurable to enable manual initiation of the test mode of operation (such as, for example, by the user's manual operation of the test mode switch (not shown) of the meter device 103.

During the test mode of operation, if a faulty operation is detected, the glucose meter device 103 is configured to generate and output a corresponding respective message as such. Examples of such faulty operation includes, but not limited to, the detection of a used test strip, insufficient blood sample on the test strip, incorrect insertion of the test strip into the test strip connector unit 202 of the meter device 103, or when the coulometer circuits are not ready for sample processing. The outputted message to the user alerting of the faulty operation may include an audible sound, a visual display, or a combination of both.

Upon successfully collecting sufficient blood sample for processing from the user 101 (FIG. 1), the glucose meter device 103 is configured to process the collected sample, and to generate a corresponding blood glucose data for output display to the user 101 on the user interface unit 203. The blood glucose data may be, for example, displayed in units of mg/dL or in units of mmol. Moreover, in one embodiment, the meter device 103 may also be configured to display the time and date information corresponding to the blood glucose level test. Moreover, the central processing unit 206 is further configured to store the processed and displayed blood glucose data in the storage unit 207.

Referring still to FIG. 2, in the configuration mode of operation, in one embodiment of the present invention, the user 101 may select and input certain predetermined parameters into the glucose meter device 103 to configure the meter device 103 for subsequent use thereafter. For example, such configurable parameters include the displayed date and time information, the alarm settings on the glucose meter device 103, the preferred display format for data display on the display unit of the user interface unit 203 in the meter device 103, the concentration unit of the generated glucose level, and an average glucose level information based on a user selected number of days such as 14-day or 30 day average of stored results.

In the measurement log review mode of operation discussed above, the glucose meter device 103 is configured to display a glucose summary (that is, the average glucose level information) of stored results, as well as other parameters such as the number of measurements incorporated into the displayed average level, and a visual indication to the user that the displayed data is the average glucose level information, and not a specific sampled glucose level data. As will be discussed in further detail below, the glucose meter device 103 may be configured to enter the measurement log review mode of operation upon the operation of the mode switch (in the user interface unit 203) while the meter device 103 is in the default clock mode.

In one embodiment, the glucose meter device 103 may be configured so that a "LO" is displayed for measured glucose values which are below 20 mg/dL, and in contrast, a "HI" is displayed when the measured glucose value exceeds 500 mg/dL. Furthermore, the meter device 103 may be configured to display the processed glucose level within approximately 15 seconds from the sampling of the corresponding blood for samples below 200 mg/dL when measured at room temperature and humidity.

Figure 3:
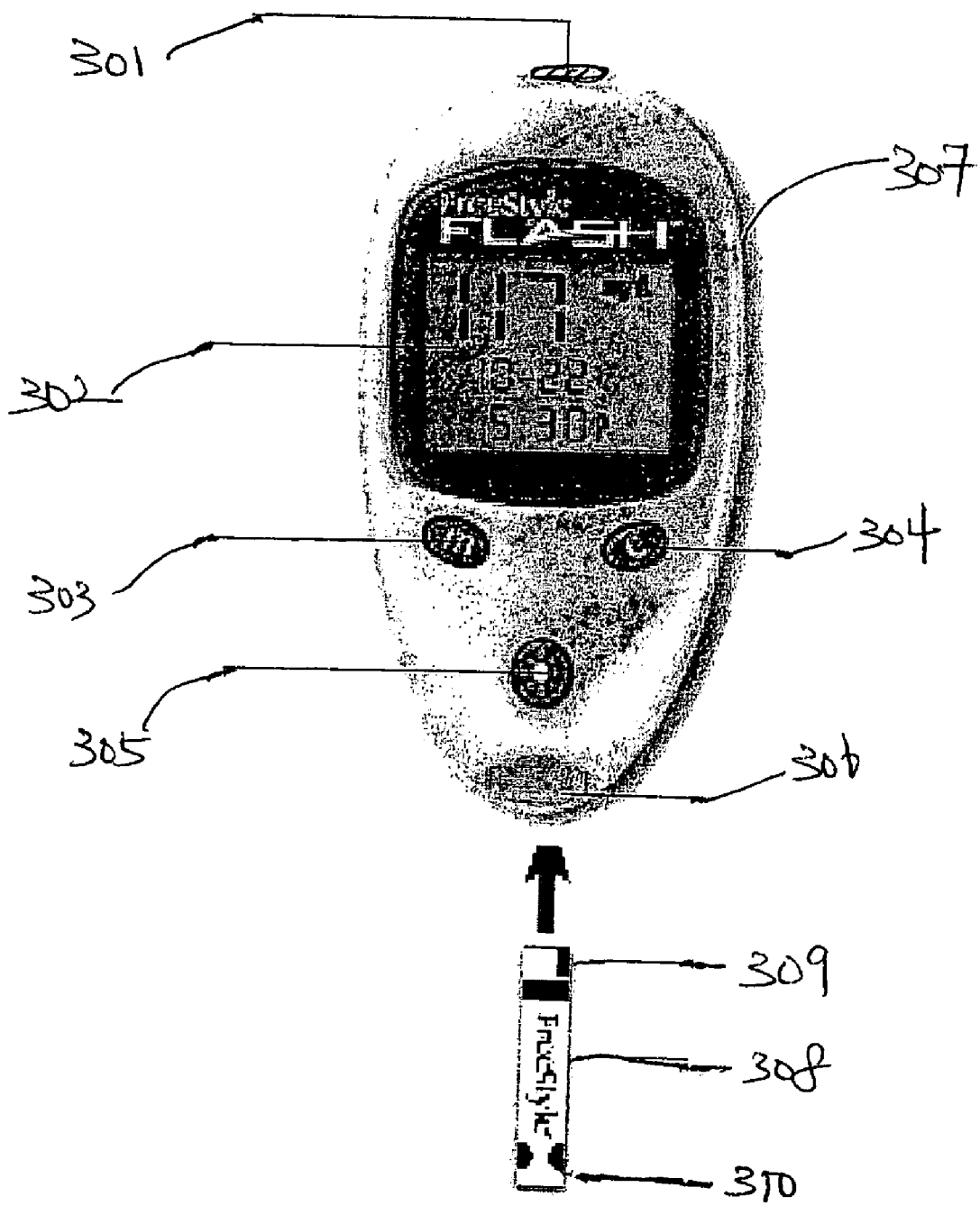
FIG. 3 illustrates the glucose meter device of FIG. 2 in accordance with one embodiment of the present invention.

FIG. 3 illustrates the glucose meter device of FIG. 2 in accordance with one embodiment of the present invention. As shown, the glucose meter device 103 includes a housing 307 which substantially encases the meter device 103. In one embodiment, the glucose meter device 103 may be physically configured such that it is 3.12 inches in length, 2.25 inches in width and 0.85 inches in height, with no more that 1.4 ounces in weight with the batteries installed. Moreover, the material used for the housing 307 may comprise plastic, metal, polymer, or a combination of any suitable material which provides substantial physical integrity when subject to normal usage of the meter device 103 including occasional dropping and other physical impacts.

Also shown in FIG. 3 is a data port 301 which corresponds to the I/O interface unit 205 (FIG. 2), and is configured to operatively couple to an external computer or data processing device to transfer data collected and processed by the glucose meter device 103. The data port 301 in one embodiment may include one of a Universal Serial Bus (USB) port, an infrared data communication port, a Bluetooth communication port, and a Wi—Fi wireless data communication port (for example, IEEE 802.11 or its equivalents).

Referring back to FIG. 3, provided on the housing 307 is a display screen 302 which may be configured to display the test results and other parameters and information such as time and data information and the like. The display screen 302 in one embodiment may include a built-in display backlight for use in low-light conditions, and may be configured to automatically switch on in low-light settings for a predetermined period of time (such as 1 minute, for example), or may be configured for manual user operation.

Also shown in FIG. 3 are three input switches—a mode switch 303, the configuration switch 304, and the light switch 305. In one embodiment, the mode switch 303 may be operated by the user to toggle between different operation modes such as the test mode, and the clock mode (default), configuration mode, and the measurement log review mode, each discussed above. The configuration switch 304 may be configured to, for example, mark a test result as control solution, change the test strip code, time and alarm settings, the output sound options, date information, the measurement unit information, and for review of the stored sample results. Also, the configuration switch 304 may also be depressed to silence the output of an alarm. Finally, the light switch 305 is configured to control the operation of the backlight of the display screen 302, as well as the flashlight function of the meter device 103.

Referring yet again to FIG. 3, a test strip port 306 is additionally provided on the housing 307 of the glucose meter device 103, and is configured to receive the insertion of a test strip 308. In one embodiment, the test strip port 306 substantially corresponds to the test strip connector unit 202 shown in FIG. 2. Also provided on the test strip port 306 is a light source such as a light emitting diode (LED) and the like which is configured to switch on and off under the operation of, for example, the light switch 305, or alternatively, in accordance with a certain operations of the glucose meter device 103 such as, for example, the detection of the test strip 308 at the opening of the test strip port 306. As can be further seen, the test strip 308 may include a top portion 309 and a bottom portion 310 such that the top portion 309 is configured to be inserted into the test strip port 306 of the glucose meter device 103, while the bottom portion 310 of the test strip 308 substantially comprises the blood sample target areas for the user to apply the blood sample or a control solution thereto. In one embodiment, the test strip 308 is a Freestyle® Test Strip currently available from the assignee of the present application, TheraSense, Inc. of Alameda, Calif.

FIGS. 4A and 4B illustrate the display screen of the glucose meter device in accordance with one embodiment of the present invention. Referring to the Figures, the display screen 302 of the glucose meter device shown in FIG. 3 includes a plurality of visual representation of display information. For example, as shown in FIG. 4A, the check owner's manual symbol 401 is displayed to alert the user 101 (FIG. 1) to refer to the manual of the glucose meter device, and may be displayed on the display screen 302 when, for example, the meter device detects LO or HI blood glucose level, out of temperature range results, and low power state. The control solution test result symbol 302 is displayed to alert the user that the user has marked a test result as a control solution test.

Referring back to FIG. 4A, the message area 403 of the display screen 302 may be configured to display information such as the date information, the time information, the number of tests performed, and other information related to the operation and function of the glucose meter device. There is also provided in the display screen 302 a test result area 406 which is configured to display the resulting glucose level determined from the corresponding blood sample. Also shown in FIG. 4A are a battery symbol 405 and a memory mode symbol 404, where the battery symbol 405 is configured to be illuminated when the power supply level (e.g., the battery level) is detected to be lower than the optimum operating level, and to alert the user 101 (FIG. 1) to replace the same. The memory mode symbol 404 on the other hand, is configured to display to the user 101 (FIG. 1) that the test result displayed in the rest result area 406 has been stored in the memory (the storage unit 207 (FIG. 2)) of the glucose meter device. In one embodiment, the memory capacity of the meter device may store up to approximately 250 blood glucose test results.

Referring now to FIG. 4B, the display screen 302 may further be configured to display a blood drop symbol and a test strip symbol 414, which are configured to operate in tandem to alert the user that the meter device is ready to apply the blood sample or the control solution. Moreover, the unit symbol 413 is configured to appear with the test result data displayed in the test result area 406 of the display screen 302 when the blood sample has been successfully collected and a corresponding glucose level has been determined based on the collected blood sample. The date setup symbol 407 on the display screen 302 may be displayed in the configuration mode when the user is setting the date information of the glucose meter device.

As further shown, a check and set test strip code symbol 408 is provided on the display screen 302 to alert the user to check and set the test strip code, while the thermometer symbol 409 is displayed on the display screen 302 when the meter is operating in a temperature range that is beyond that which will permit an accurate reading. A set of sound level symbols 410 are provided in one embodiment to indicate whether the glucose meter device audible output alert mode is at a predetermined setting (for example, high, low or off), while the time set symbol 411 appears on the display screen 302 in the default clock mode when the user is setting the time information on the glucose meter device. Finally, the data average symbol 412 is configured to appear on the display screen 302 with a glucose reading that is the average value of the readings from the past 14 days, for example or any other predetermined time period as may be established by the meter device as a default mode or by the user during calibration stage of the glucose meter device.

In the preferred embodiment of the present invention, when the meter 103 is not otherwise in use, the current date is continuously displayed on the upper line (top row of five 7-segment digits) of message area 403, and the current time is continuously displayed on the lower line (bottom row of five 7-segment digits) of message area 403. As previously mentioned, immediately after a blood glucose test is completed, the numerical result is shown in the test result area 406. In this preferred embodiment, the date and time information are displayed in a different area of display screen 302 from the glucose test results, and with different sized digits (preferably smaller as shown). Also, it is preferable that the test result area 406 be offset from the center of display screen 302, even more preferably located in a corner of the display screen 302 as shown.

In the manner described above, the display screen 302 of the glucose meter device in accordance with one embodiment of the present invention may be configured to display information corresponding to the glucose tests and the processed results in a easy and intuitive manner.

Figure 5:
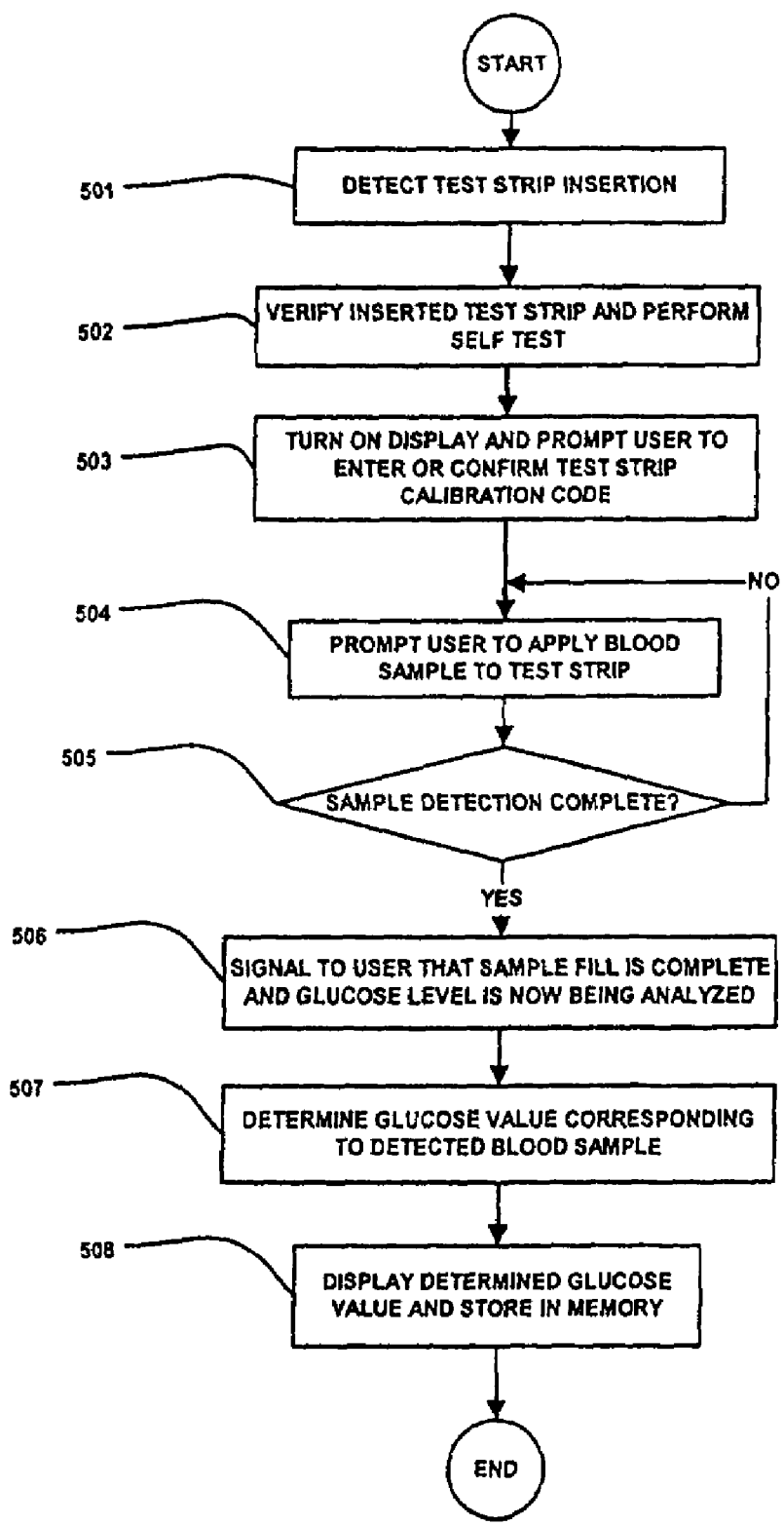
FIG. 5 is a flowchart illustrating the procedure for performing a blood glucose test using the glucose meter device in accordance with one embodiment of the present invention.

FIG. 5 is a flowchart illustrating the procedure for performing a blood glucose test using the glucose meter device in accordance with one embodiment of the present invention. Referring to FIGS. 2 and 5, at step 501, the glucose meter device detects the insertion of a test strip 102 in the test strip connector unit 202 (FIG. 2). In response to the detection of the test strip 102 insertion, the meter device 103 is powered on, and at step 502, the inserted test strip is verified and a self test of the meter device is performed. More specifically, at step 502, a system check illumination briefly lights up the entire display screen 302 and the various data symbols and areas included therein, and thereafter, in step 503 the user 101 is prompted to input a code number which corresponds to the calibration code number preassigned to the test strip inserted into the meter device.

After verifying the code number for the test strip, at step 504, the blood drop and test strip symbols 414 (FIG. 4B) are displayed on the display screen 302 to prompt the user to apply the blood sample to the test strip. When the blood sample is in contact with the test strip, the test strip acts like a sponge and pulls the blood into the strip through its edges. Thereafter at step 505, it is determined whether the collected blood sample amount is sufficient to generate a corresponding blood glucose level. If it is determined at step 505 that the collected blood sample amount is not sufficient to generate the corresponding blood glucose level, then the procedure returns to step 504 to prompt the user to further apply the blood sample to the test strip.

On the other hand, if it is determined at step 505 that the collected level of blood sample is sufficient to generate the corresponding blood glucose level, the user 101 (FIG. 1) is notified as such in step 506 by an audible alert sound output via the user interface 203 (e.g., through an output speaker), and/or by visual display on the display screen 302 (FIG. 3). The glucose meter device is then configured at step 507 to determine the glucose value corresponding to the detected blood sample, and thereafter at step 508, to display the resulting glucose value on the display screen 302 (FIG. 3), and to store the generated glucose value in the storage unit 207 (FIG. 2).

In one embodiment, the glucose meter device may be configured to output a single audible alert notification when the collected blood sample is sufficient to generate the corresponding glucose level information, and to output a double audible alert notification when the glucose level information has been determined and displayed on display screen 302. Additionally, in one embodiment, the time and date information may also be displayed on the display screen 302 in connection with the generated glucose level information.

In accordance with another embodiment, the glucose meter device may be configured such that upon power on procedure, the light source (e.g., an LED) at the test strip port 306 (FIG. 3) is configured to illuminate at substantially 50% of the full intensity to permit the introduction of the test strip 102 into the test strip port 306. Thereafter, when the test strip 102 is fully inserted into the test strip port 306 of the glucose meter device, the light source at the test strip port 306, and alternatively, in addition to the backlight of the display screen 302, is illuminated at the full intensity level to indicate blood sample collection operation.

Figure 6:
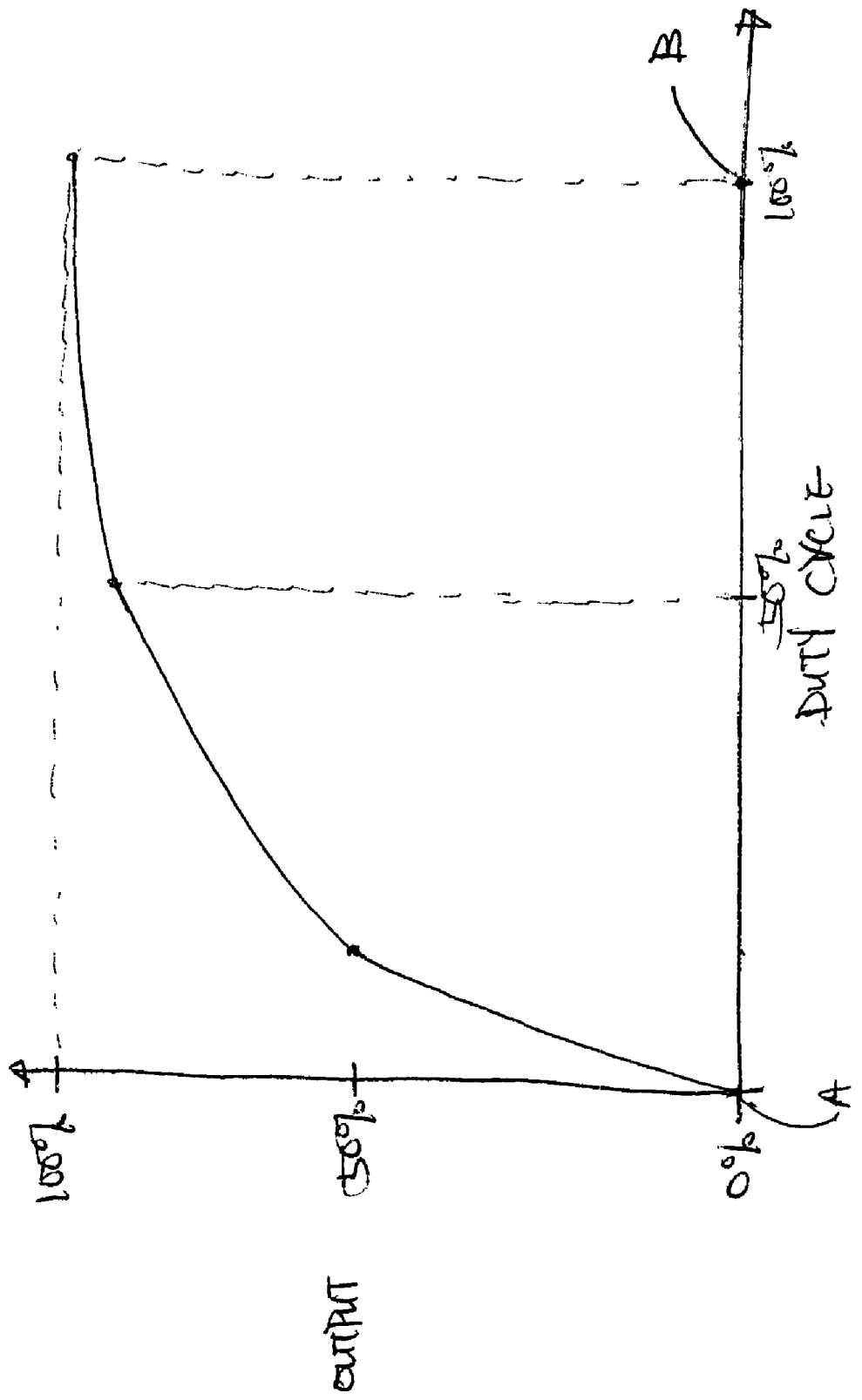
FIG. 6 illustrates the output LED power level as a function of the power state in accordance with one embodiment of the present invention.
Figure 3:
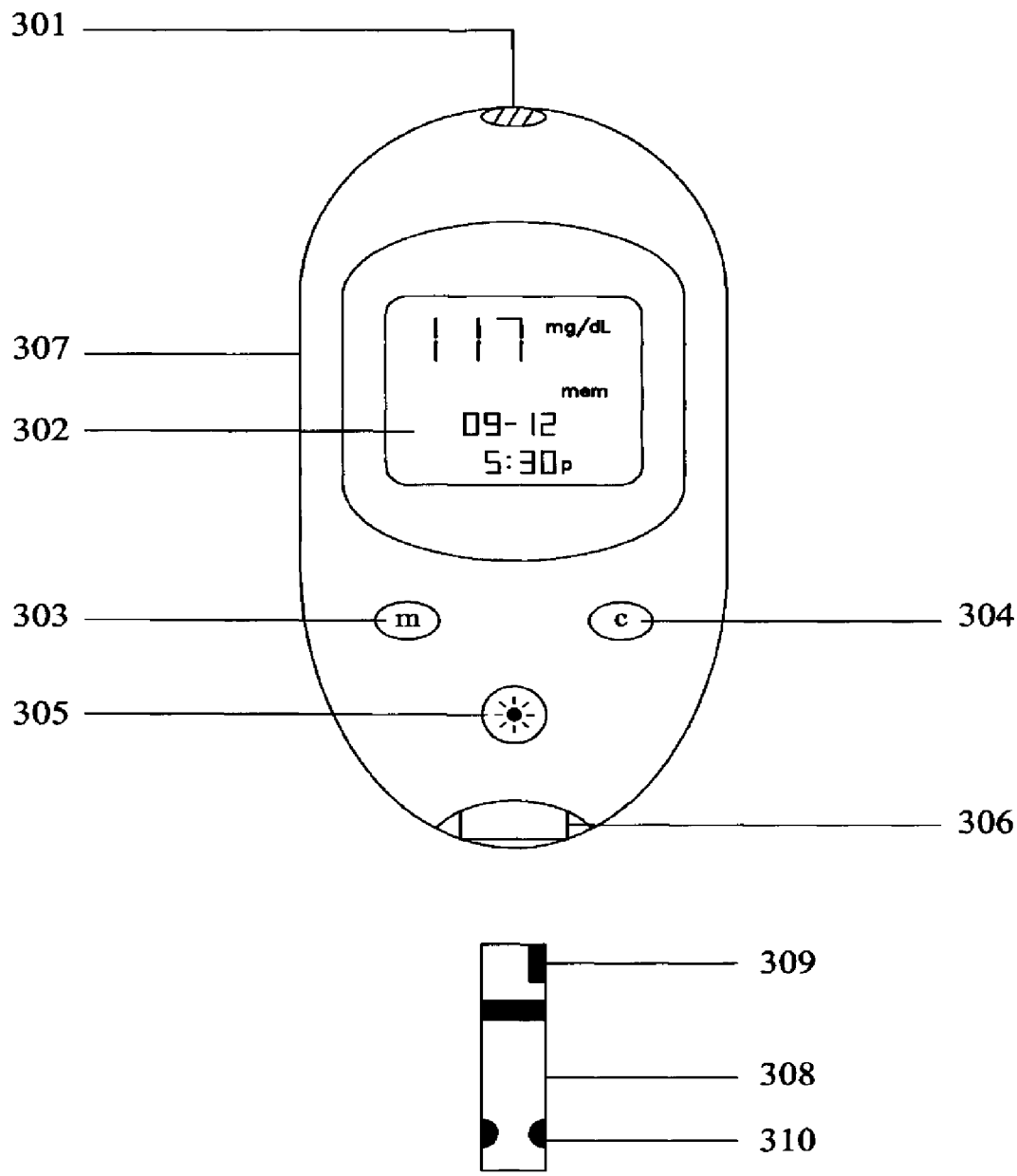

When the collection of the blood sample is concluded, the intensity of the light source at the test strip port 306 (and alternatively, as well as the backlight of the display screen 302) are reduced substantially to the 50% level again, and when the test strip is removed from the test strip port 306, the light source is configured to shut off completely. Indeed, as the light source (e.g., the LED) may be pulsed and still display substantially the same light output as one which is turned on in steady state, the battery life of the glucose meter device may be prolonged since the pulsed LED light source requires significantly less power (and thus draining the battery at a much slower rate) than when the LED light source is maintained at the on position. Indeed, in one embodiment, the central processing unit 206 of the glucose meter device 103 may be configured to control the switching on and off of the light source as well as the level of light intensity by, for example, adjusting the duty cycle and the period during which the light source is configured to be turned on. For example, FIG. 6 illustrates the output LED power level as a function of the power state in accordance with one embodiment of the present invention. As can be seen from the Figure, 50% duty cycle as shown on the X-axis corresponds to approximately 80% of the output power level for the LED light source.

In a preferred embodiment, a yellow/green LED is used for the test strip light, such as part number LT19209-40 manufactured by Ledtech Electronics Corporation located in Hsin-Tien, Taiwan, or part number ZSG56W manufactured by SunLED Co. located in Kowloon, Hong Kong. These LEDs provide a light having a peak wavelength of about 575 nanometers, which has been found to provide optimal contrast between various colors of blood against various skin pigments in low light conditions. More specifically, using a yellow-green LED with peak wavelength of 570 nanometers in one embodiment provided optional contrast between the various colors of blood against the skin pigments in low light conditions.

Also, preferably, the test light LED is pulsed faster than 60-100 hertz so that it appears to the human eye that it is continuously on without flickering, most preferably 3 or 7 khz. It has been discovered that a 10% duty cycle with the LEDs specified above provides the most desired balance between light intensity and battery power savings. A brighter light output than this can be disruptive in certain low light settings, such as a movie theater, and can inhibit inconspicuous blood glucose testing.

In an alternate embodiment of the present invention, the glucose meter device may be configured such that the backlight on the display screen 302 is turned on when the test strip 102 is inserted into the test strip port 306 of the meter device. Thereafter, the backlight is configured to turn off when the blood drop and test strip symbols 414 are displayed in tandem to alert the user that the meter device is ready to apply the blood sample or the control solution. At the same time that the backlight is turned off, the light source at the test strip port 306 (e.g., the LED light source) is illuminated so that the user may light up the test strip 102 and the sample acquisition site on the user 101 if desired. Thereafter, when the meter device detects a sufficient level of blood sample on the test strip 102 (i.e., step 505 (FIG. 5) is successfully performed), the light source at the test strip port 306 is disabled, and the backlight on the display screen 302 is once again illuminated so that the user may view the corresponding glucose level generated from the collected blood sample.

In a slightly different embodiment, pressing the light button 305 powers on either the display backlight or the test strip light, depending on what mode the meter is in. Pressing the light button 305 in non-test modes powers on the display backlight. The display backlight goes out when light button 305 is pressed again, or when the meter is inactive for 5 seconds. Pressing the light button when the blood drop and test strip symbols appear on the display screen powers on the test strip light. The test strip light goes out when the light button 305 is pressed again, or the meter receives the correct amount of blood for the test (i.e. the test strip is filled), or after 60 seconds of meter inactivity, or when the test strip is removed from the meter. Thus, in this embodiment, the test strip light cannot be activated unless there is a test strip inserted in the test strip port. If either the test strip light or the display backlight is used during the test mode, the backlight preferably powers on to show the test results after the measurement is complete.

Preferably, the glucose meter is powered by two coin cell batteries of a common size, such as CR2032. It is also preferable that one of the batteries is dedicated to powering the test strip light and display backlight, and the other is dedicated to powering the meter's processor and other functions. It may also be desirable to allow the meter to be placed in a "shelf mode" after final testing at the factory such that even with batteries inserted, nothing is shown on the display and the processor is in an energy saving sleep mode until one of the buttons is pressed or a test strip is inserted in the meter to resume normal operation.

In the manner described above, in accordance with the various embodiments of the present invention, the glucose meter device 103 is configured such that it is simple, intuitive and easy to use, permitting the user to perform the tests relatively discreetly, and is also easily used by third parties such as the user's physician, nurse, care giver or family member. Moreover, given the compact physical configuration, the glucose meter device 103 is substantially small, compact, sleek and readily portable by the user.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An apparatus, comprising:
    a compact housing including a blood glucose meter interface;
    a display unit coupled to the housing, the display unit configured to display information related to a blood glucose measurement and including a light source to illuminate the display unit;
    an input unit disposed on the housing, the input unit configured to provide one or more input functions;

a power source provided within the housing for providing power to the display unit;
an RF receiver provided in the housing and configured to receive a plurality of signals associated with a monitored analyte level from an analyte sensor; and
a processing unit disposed within the housing to control the level of light intensity of the display light source;
wherein the display unit is illuminated by the light source at a reduced intensity during a first portion of the operation and at a full intensity during a second portion of the operation; and further
wherein the display unit displays data associated with the monitored analyte level.

2. The apparatus of claim 1 wherein the display unit includes one of a liquid crystal display (LCD), a touch sensitive screen, or a plasma display unit.

3. The apparatus of claim 1 wherein the light source is configured to provide one or more of a backlight function or a flashlight function of the display unit.

4. The apparatus of claim 1 wherein the light source is configured to be pulsed at a frequency greater than approximately 60-100 Hertz.

5. The apparatus of claim 1 wherein the light source includes a light emitting diode (LED).

6. The apparatus of claim 5 wherein the LED is a yellow-green LED.

7. The apparatus of claim 1 further including a lancing device operatively coupled to the compact housing.

8. An apparatus, comprising:
a compact housing including a apparatus interface;
a display unit coupled to the housing, the display unit configured to display information related to a blood glucose measurement determined based on a fluid sample received at the apparatus interface, the display unit including a light source including a light emitting diode (LED) pulsed at a predetermined frequency;
an input unit disposed on the housing, the input unit configured to provide one or more input functions;
a power source provided within the housing for providing power to the display unit;
a communication port provided in the housing and configured to communicate the blood glucose measurement to a remote location; and
a processing unit disposed within the housing to control the level of light intensity of the display light source, wherein the display unit is illuminated by the light source at a reduced intensity during a first operation and at a full intensity during a second operation.

9. The apparatus of claim 8 wherein the display unit includes one of a liquid crystal display (LCD), a touch sensitive screen, or a plasma display unit.

10. The apparatus of claim 8 wherein the display unit includes a light source to illuminate the display unit.

11. The blood glucose meter of claim 8 wherein the light source is configured to provide a backlight function or a flashlight function of the display unit.

12. The apparatus of claim 8 further including a lancing device operatively coupled to the compact housing.

13. An apparatus, comprising:
a compact housing including a apparatus interface;
a display unit coupled to the housing, the display unit displaying information related to a blood glucose measurement;
an input unit disposed on the housing, the input unit providing one or more input functions;
a power source provided within the housing for providing power to the display unit; and
a processing unit disposed in the housing and operatively coupled to the display unit and the input unit, the processing unit controlling the information displayed on the display unit in response to at least one of the one or more input functions, the processing unit further configured to analyze one or more analyte related data received from an in vivo analyte sensor;
wherein the housing includes a port integrated on said housing configured to receive a blood glucose test strip; and further
wherein the port includes a light source to substantially illuminate the port, the processing unit controlling the level of light intensity of the light source, wherein the port is illuminated at a full intensity or at a reduced intensity, respectively, during the test strip insertion into and removal from the port.

14. The apparatus of claim 13, wherein the light source of the port is configured to illuminate a blood sample acquisition site.

15. The apparatus of claim 14 wherein the blood sample acquisition site is located substantially on the surface of a patient's skin.

16. The apparatus of claim 15 wherein the surface of the patient's skin is positioned substantially at a predetermined angle from the direction of illumination from the port light source.

17. The apparatus of claim 16 wherein the predetermined angle is less than 90 degrees.

18. The apparatus of claim 14 wherein the blood sample acquisition site is illuminated only during a sample acquisition process.

19. The apparatus of claim 13 wherein the display unit is configured to illuminate upon detection of a blood glucose test strip insertion into the port.

20. The apparatus of claim 19 wherein the display unit is configured to remain illuminated until the test strip is removed from the port.

21. The apparatus of claim 13 wherein the input unit includes an on/off switch.

22. The apparatus of claim 13 further including a lancing device operatively coupled to the compact housing.

23. An apparatus, comprising:
a compact housing including a apparatus interface;
a display unit coupled to the housing, the display unit including a display light source to illuminate the display unit;
an input unit coupled to the housing, the input unit configured to provide one or more input functions;
a power source provided within the housing for providing power to the display unit; and
a processing unit disposed in the housing and operatively coupled to the display unit and the input unit, the processing unit controlling the information displayed on the display unit in response to at least one of the one or more input functions, the processing unit analyzing one or more analyte related data received from an in vivo analyte sensor, and controlling the level of intensity of the display light source;
wherein the display unit is illuminated by the display light source at a reduced intensity during a first operation and at a full intensity during a second operation; and further
wherein the housing includes a port integrated on said housing to receive a blood glucose test strip, the port coupled to the apparatus interface.

24. The apparatus of claim 23 wherein the display unit includes one of a liquid crystal display (LCD), a touch sensitive screen, and a plasma display unit.

25. The apparatus of claim 23 wherein the display light source is configured to provide at least one of a backlight function or a flashlight function of the display unit.

26. The apparatus of claim 23 wherein the display light source includes a light emitting diode (LED).

27. The apparatus of claim 23 further including a lancing device operatively coupled to the compact housing.

28. An apparatus, comprising:
a compact housing including a glucose meter interface;
a processing unit disposed in the housing to process one or more signals generated based on a fluid sample received by the glucose meter interface, the processing unit calibrating one or more analyte related data received from an in vivo analyte sensor based on the processed one or more signals generated based on the fluid sample;
a display unit coupled to the housing, the display unit including a display light source to illuminate the display unit, the processing unit controlling the level of intensity of the display light source wherein the display unit is illuminated at a reduced intensity during a first operation of the processing unit and at a full intensity during a second operation of the processing unit;
an input unit coupled to the housing, the input unit configured to provide one or more input functions; and
a power source provided within the housing for providing power to the processing unit and the display unit.

29. The apparatus of claim 28 wherein the display unit includes one of a liquid crystal display (LCD), a touch sensitive screen, or a plasma display unit.

30. The apparatus of claim 28 wherein the display light source is configured to provide one or more of a backlight function or a flashlight function of the display unit.

31. The apparatus of claim 28 wherein the display light source includes a light emitting diode (LED).

32. The apparatus of claim 28 further including a lancing device operatively coupled to the compact housing.

33. An apparatus, comprising:
a compact housing including a apparatus interface;
a processing unit disposed in the housing and processing one or more signals generated based on a fluid sample received by the glucose meter interface, the processing unit calibrating one or more analyte related data received from an in vivo analyte sensor based on the processed one or more signals generated based on the fluid sample;
a display unit coupled to the housing, the display unit including a display light source to illuminate the display unit, wherein the processing unit controls the level of intensity of the light source, wherein the display unit is illuminated at a reduced intensity during a first operation and at a full intensity during a second operation;
an input unit coupled to the housing, the input unit configured to provide one or more input functions; and
a power source provided within the housing for powering the processing unit and the display unit;
wherein the housing includes a port integrated on said housing configured to receive a blood glucose test strip; and further
wherein the port includes a port light source, the port light source configured to substantially illuminate the port to assist in the insertion and/or removal of the blood glucose test strip, the processing unit controlling the intensity of the port light source, wherein the port is illuminated at a full intensity and at a reduced intensity, respectively, during the test strip insertion into and removal from the port.

34. The apparatus of claim 33 wherein the display unit includes one of a liquid crystal display (LCD), a touch sensitive screen, or a plasma display unit.

35. The apparatus of claim 33 wherein the display light source is configured to provide one or more of a backlight function or a flashlight function of the display unit.

36. The apparatus of claim 33 wherein the display light source includes a light emitting diode (LED).

37. The apparatus of claim 33 wherein the port light source is integrated with the display light source.

38. The apparatus of claim 33 wherein the display unit is configured to illuminate upon detection of a blood glucose test strip insertion into the port.

39. The apparatus of claim 38 wherein the display unit is configured to remain illuminated until the test strip is removed from the port.

40. The apparatus of claim 33 wherein the port light source is configured to illuminate a blood sample acquisition site.

41. The apparatus of claim 40 wherein the blood sample acquisition site is located substantially on the surface of a patient's skin.

42. The apparatus of claim 41 wherein the surface of the patient's skin is positioned substantially at a predetermined angle from the direction of illumination from the port light source.

43. The apparatus of claim 42 wherein the predetermined angle is less than 90 degrees.

44. The apparatus of claim 40 wherein the blood sample acquisition site is illuminated only during a sample acquisition process.

45. The apparatus of claim 33 further including a lancing device operatively coupled to the compact housing.

46. A method, comprising:
providing a compact housing;
disposing a display unit on the housing, the display unit including a display light source to illuminate the display unit, the light source illuminating the display unit at a reduced intensity during a first operation, and at a full intensity during a second operation;
detecting a presence of an analyte test strip in a strip port coupled to the housing and generating a measurement data based on a fluid sample on the test strip in the strip port;
receiving a plurality of time spaced signals associated with a monitored analyte level; and
processing the received plurality of time spaced signals based on the generated measurement data.

47. The method of claim 46 including illuminating a sample acquisition site from the strip port.

48. The apparatus of claim 1, wherein the processing unit is configured to control the level of light intensity of the display light source by one or more of adjusting the duty cycle of the light source and adjusting the period during which the light source is turned on.

49. The apparatus of claim 8, wherein the processing unit is configured to control the level of light intensity of the display light source by one or more of adjusting the duty cycle of the light source and adjusting the period during which the light source is turned on.

50. The apparatus of claim 13, wherein the processing unit is configured to control the level of light intensity of the port light source by one or more of adjusting the duty cycle of the light source and adjusting the period during which the light source is turned on.

51. The apparatus of claim 23, wherein the processing unit is configured to control the level of light intensity of the display light source by one or more of adjusting the duty cycle of the light source and adjusting the period during which the light source is turned on.

52. The apparatus of claim 28, wherein the processing unit is configured to control the level of light intensity of the display light source by one or more of adjusting the duty cycle of the light source and adjusting the period during which the light source is turned on.

53. The apparatus of claim 33, wherein the processing unit is configured to control the level of light intensity of the display and port light sources by one or more of adjusting the duty cycle of the respective light source and adjusting the period during which the respective light source is turned on.

54. The method of claim 46, wherein illuminating the display unit at reduced intensity includes one or more adjusting the duty cycle of the light source and adjusting the period during which the light source is turned on.

\* \* \* \* \*

UNITED STATES PATENT AND TRADEMARK OFFICE
CERTIFICATE OF CORRECTION

| | | |
|---|---|---|
| PATENT NO. | : 8,071,028 B2 | |
| APPLICATION NO. | : 10/861626 | |
| DATED | : December 6, 2011 | |
| INVENTOR(S) | : Tae Wan Andrews et al. | |

It is certified that error appears in the above-identified patent and that said Letters Patent is hereby corrected as shown below:

Title Page:
Title page, Section (75) Inventors, replace "Tae Wan Andrews, Oakland, CA (US)" with
--Tae Wan Andrews, San Diego, CA (US)--
Title page, Section (75) Inventors, replace "Hyong Yoon Park, San Francisco, CA (US)" with
--Hyoung Yoon Park, Duluth, GA (US)--

Signed and Sealed this
Seventh Day of February, 2012

David J. Kappos
*Director of the United States Patent and Trademark Office*

Drawings: Sheet 3 of 6 (FIGURE 3); Delete incorrect FIGURE 3 and insert replacement FIGURE 3 attached

CERTIFICATE OF CORRECTION (continued)
U.S. Pat. No. 8,071,028 B2

Drawings: Sheet 4 of 6 (FIGURES 4A and 4B): Delete incorrect FIGURES 4A and 4B and insert replacement FIGURES 4A and 4B shown below

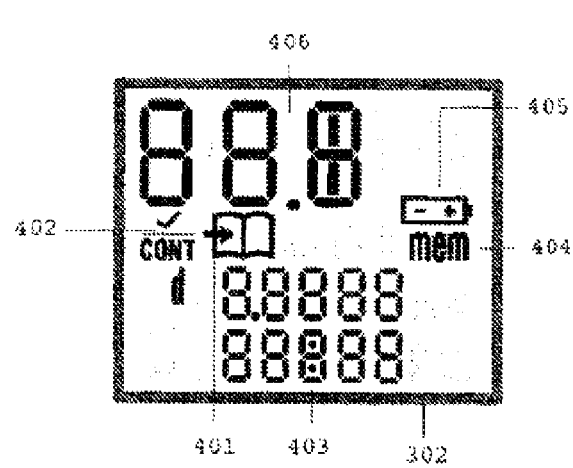
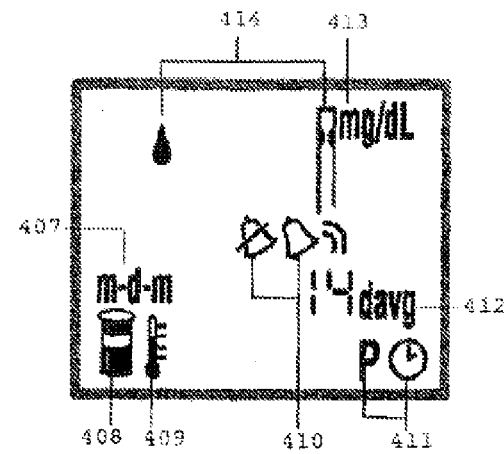

FIGURE 4A

FIGURE 4B

Drawings: Sheet 6 of 6 (FIGURE 6): Delete incorrect FIGURE 6 and insert replacement FIGURE 6 shown below

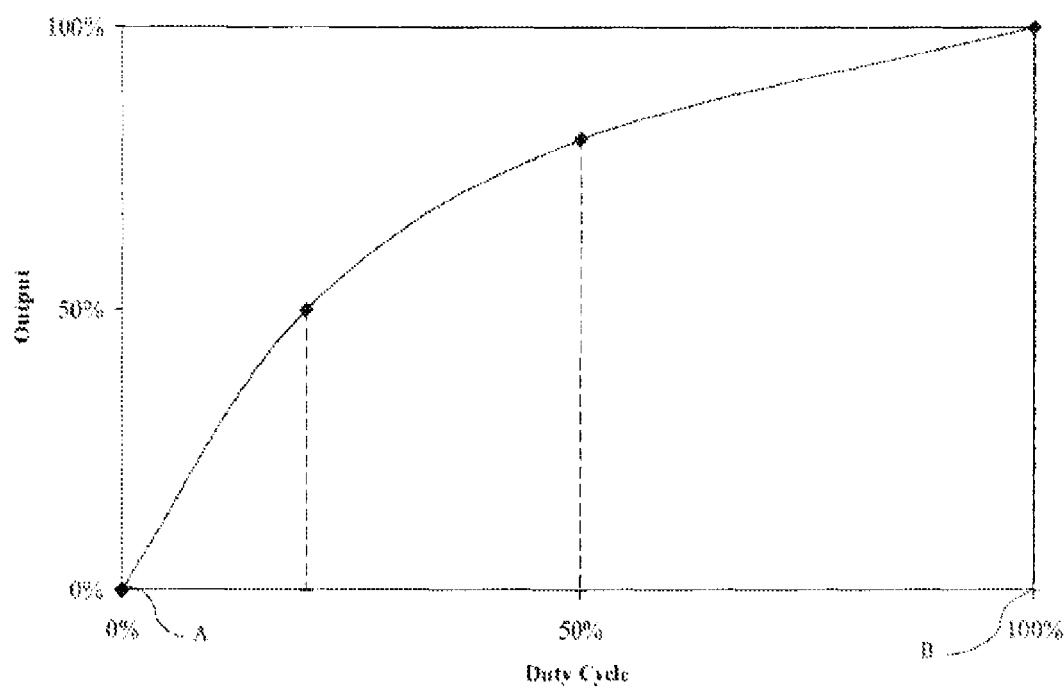

FIGURE 6

CERTIFICATE OF CORRECTION (continued)
U.S. Pat. No. 8,071,028 B2

Specification:
Column 4, line 1, replace "along" with --alone--
Column 9, line 4, replace "glucose meter device" with --glucose meter device 103--
Column 9, line 12, replace "test result symbol 302" with --test result symbol 402--
Column 9, line 29, replace "rest result area" with --test result area--
Column 10, line 11, replace "in a comer" with --in a corner--
Column 10, line 14, replace "glucose meter device" with --glucose meter device 103--
Column 11, lines 7-8, replace "glucose meter device" with --glucose meter device 103--
Column 11, line 64, replace "meter device" with --meter device 103--

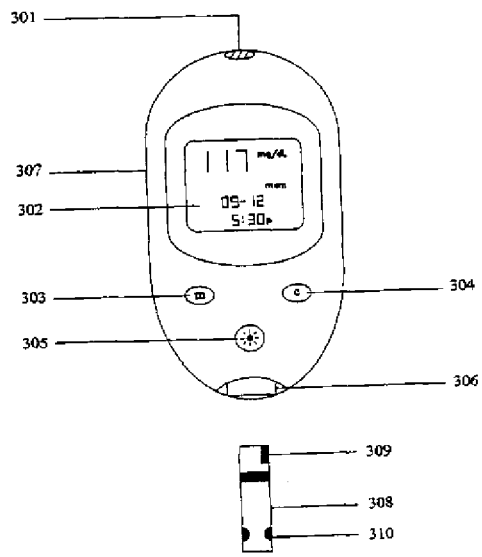

Claims:
Column 13, line 3, replace "RE receiver" with --RF receiver--
Column 13, line 30, replace "apparatus interface" with --blood glucose meter interface--
Column 13, line 34, replace "apparatus interface" with --blood glucose meter interface--
Column 13, line 60, replace "apparatus interface" with --blood glucose meter interface--
Column 14, line 45, replace "apparatus interface" with --blood glucose meter interface--
Column 14, line 67, replace "apparatus interface" with --blood glucose meter interface--
Column 15, line 42, replace "apparatus interface" with --blood glucose meter interface--

(12) United States Patent
Andrews et al.

(10) Patent No.: US 8,071,028 B2
(45) Date of Patent: Dec. 6, 2011

(54) METHOD AND APPARATUS FOR PROVIDING POWER MANAGEMENT IN DATA COMMUNICATION SYSTEMS

(75) Inventors: Tae Wan Andrews, Oakland, CA (US); Stephen C. Bubrick, Orinda, CA (US); Sheilah S. Estoesta, Mountain View, CA (US); Brad D. Etter, Fremont, CA (US); Hyong Yoon Park, San Francisco, CA (US); Gene Ming Pon, San Jose, CA (US); Christopher V. Reggiardo, Castro Valley, CA (US); Heber Saravia, Daly City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1113 days.

(21) Appl. No.: 10/861,626

(22) Filed: Jun. 4, 2004

(65) Prior Publication Data
US 2005/0009126 A1    Jan. 13, 2005

Related U.S. Application Data

(60) Provisional application No. 60/478,436, filed on Jun. 12, 2003.

(51) Int. Cl.
*G01N 33/00* (2006.01)
(52) U.S. Cl. ....... 422/68.1; 422/50; 422/82.05; 422/104
(58) Field of Classification Search ............... 422/68.1, 422/50, 82.05, 104; 364/413.02
See application file for complete search history.

(56) References Cited

U.S. PATENT DOCUMENTS

| | | | |
|---|---|---|---|
| 3,930,493 A | 1/1976 | Williamson | |
| 4,018,547 A | 4/1977 | Rogen | |
| 4,121,282 A | 10/1978 | Ohsawa | |
| 4,439,197 A | 3/1984 | Honda et al. | |
| 4,531,235 A | 7/1985 | Brusen | |
| 4,866,396 A | 9/1989 | Tamura | |
| 4,984,581 A | 1/1991 | Stice | |
| 5,004,532 A | 4/1991 | Hale | |
| 5,019,974 A * | 5/1991 | Beckers | 600/316 |
| 5,051,880 A | 9/1991 | Harm et al. | |
| 5,079,920 A | 1/1992 | Whitehead et al. | |

(Continued)

FOREIGN PATENT DOCUMENTS

EP   0455455   11/1991

(Continued)

OTHER PUBLICATIONS

"An Electrochemical Slow Flow Meter", http://gore.ocean.washington.edu/research/slow_flow_meter.html, Feb. 10, 2005, 3 pages.

(Continued)

*Primary Examiner* — Sam P Siefke
(74) *Attorney, Agent, or Firm* — Jackson & Co., LLP

(57) ABSTRACT

A blood glucose meter having a compact housing, a display unit disposed on the housing, the display unit including a display light source to illuminate the display unit, an input unit disposed on the housing, the input unit configured to provide input functions for the blood glucose meter, and a power source provided within the housing for providing power to the blood glucose meter, where the housing includes a port integrated on said housing configured to receive a blood glucose test strip, and corresponding methods of measuring blood glucose meter is provided.

54 Claims, 6 Drawing Sheets